United States Patent
Carls et al.

(10) Patent No.: US 8,348,954 B2
(45) Date of Patent: Jan. 8, 2013

(54) ELECTRONIC GUIDANCE OF SPINAL INSTRUMENTATION

(75) Inventors: Thomas Carls, Memphis, TN (US); Kent Anderson, Sunnyvale, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1093 days.

(21) Appl. No.: 12/211,164

(22) Filed: Sep. 16, 2008

(65) Prior Publication Data

US 2010/0069919 A1     Mar. 18, 2010

(51) Int. Cl.
*A61B 17/56* (2006.01)
(52) U.S. Cl. .................................................. 606/86 A
(58) Field of Classification Search .......... 606/246–279, 606/86 A, 86 R; 600/407, 424, 431, 433–435
See application file for complete search history.

(56) References Cited

U.S. PATENT DOCUMENTS

| | | | |
|---|---|---|---|
| 6,074,394 A * | 6/2000 | Krause | 606/86 R |
| 6,162,228 A | 12/2000 | Durham | |
| 6,261,247 B1 * | 7/2001 | Ishikawa et al. | 600/587 |
| 6,711,429 B1 | 3/2004 | Gilboa et al. | |
| 6,796,988 B2 | 9/2004 | Melkent et al. | |
| 6,911,026 B1 | 6/2005 | Hall et al. | |
| 6,969,384 B2 | 11/2005 | de Juan, Jr. et al. | |
| 7,029,478 B2 | 4/2006 | Hollstien et al. | |
| 7,060,075 B2 | 6/2006 | Govari et al. | |
| 7,197,354 B2 | 3/2007 | Sobe | |
| 2004/0034347 A1 | 2/2004 | Hall et al. | |
| 2005/0027285 A1 | 2/2005 | Ritter et al. | |
| 2005/0070916 A1 | 3/2005 | Hollstien et al. | |
| 2005/0075562 A1 | 4/2005 | Szakelyhidi, Jr. et al. | |
| 2005/0277934 A1 | 12/2005 | Vardiman | |
| 2007/0191840 A1 | 8/2007 | Pond | |
| 2007/0213714 A1 | 9/2007 | Justis | |
| 2008/0086145 A1 | 4/2008 | Sherman et al. | |
| 2008/0177278 A1 | 7/2008 | Stauch et al. | |
| 2009/0216113 A1 * | 8/2009 | Meier et al. | 600/424 |

OTHER PUBLICATIONS

International Searching Authority, ISR and Written Opinion, Mar. 15, 2010.

* cited by examiner

*Primary Examiner* — Eduardo C Robert
*Assistant Examiner* — David Comstock
(74) *Attorney, Agent, or Firm* — Dilworth & Barrese, LLP (57) ABSTRACT

Systems and methods for positioning a connecting element adjacent an anatomical structure in minimally-invasive surgical procedures, including an electronic guidance system associated with the connecting element and at least one receiving portion of a tissue anchor that receives the connecting element in the patient. The electronic guidance system includes a processor subsystem to receive signals from the guidance system and provide relative positional data between the connecting element and the at least one receiving portion to aid the surgeon in guiding the connecting element to the receiving portion. In one embodiment, the systems and methods are used in association with positioning a connecting element adjacent the spinal column in minimally-invasive spinal stabilization procedures.

27 Claims, 5 Drawing Sheets

ELECTRONIC GUIDANCE OF SPINAL INSTRUMENTATION

BACKGROUND

Various devices and methods have been used in association with minimally-invasive surgical procedures. Examples of minimally-invasive surgical procedures include stabilization techniques for stabilizing bony structures such as long bones and the spinal column. The fracture of an elongated bone, such as a femur or humerus, can be stabilized by securing a plate to the fractured bone across the fracture. The plate extends across the fractured area and stabilizes the fractured components of the bones relative to one another in a desired position. When the fracture heals, the plate can be removed or left in place, depending on the type of plate that is used. Another type of stabilization technique uses one or more elongated rods extending between components of a bony structure, such as the vertebrae of the spinal column, and secured to the bony structure to stabilize the components relative to one another. The components of the bony structure are exposed, and one or more bone engaging elements are anchored to each component. The elongated rod is then secured to the bone engaging elements in order to stabilize the components of the bony structure.

One problem associated with the above described stabilization techniques is that the skin and tissue surrounding the surgical site must be cut, removed and/or repositioned in order for the surgeon to access the location where the device is to be inserted. This repositioning of tissue causes trauma, damage and/or scarring to the tissue. There are also risks that the tissue will become infected, or that longer recovery times will be required after surgery for the tissue to heal.

Minimally-invasive surgical techniques are particularly desirable in, for example, spinal, vascular, and neurosurgical applications because of the need for access to locations deep within the body and the presence of vital intervening tissues. The development of percutaneous, minimally-invasive procedures has yielded a major improvement in reducing recovery time and post-operative pain because they require minimal, if any, muscle dissection, and can also be performed under local anesthesia. The benefits of minimally-invasive techniques have also found application in surgeries adjacent other locations in the body where it is desirable to minimize tissue disruption and/or trauma. Current techniques for inserting implants and instrumentation utilize X-ray, fluoroscopic and/or magnetic resonance imaging to provide bi-planar visualization of the target location and of the implanted objects. However, these techniques can present difficulties for the surgeon in interpreting the relative three-dimensional location of the objects and instrumentation during the implantation procedure.

Thus, there remains a need for further improvements in instruments and methods for minimally-invasive surgical techniques that aid the surgeon in positioning implants, devices and instrumentation at desired locations within the body of the patient.

SUMMARY

Systems and methods for positioning a connecting element adjacent an anatomical structure in minimally-invasive surgical procedures include an inserter instrument and one or more anchors engageable to anatomical tissue. The inserter instrument can be engaged to the connecting element and utilized to insert the connecting element through tissue of the patient in a minimally-invasive surgical procedure to a location adjacent to one or more of the anchors. An electronic guidance system includes a targeting device associated with the anchor, and a tracking device associated with the connecting element. The targeting and tracking devices communicate with one another to provide signals indicative of the relative positions between the connecting element and anchor to assist the surgeon in guiding the connecting element toward the anchor through tissue of the patient in a minimally-invasive surgical procedure.

Related features, aspects, embodiments, objects and advantages will be apparent from the following description.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Systems and methods for insertion of a connecting element for connection with one or more anchors engaged to anatomical tissue are provided. In one form, the systems include at least one anchor extension extending from at least one anchor engaged to a component of an anatomical structure. In other forms, extensions are not provided for one or more of the anchors. An inserter instrument is engaged to the connecting element. An electronic guidance system associated with the anchor and the connecting element provides the surgeon with relative positional data between the connecting element and the at least one anchor to assist the surgeon in guiding the connecting element to the anchor through tissue of the patient. The relative positional data includes, but is not limited to, an indication that the connecting element is moving toward or away from the anchor. Once the connecting element is in its proper position adjacent to or within the anchor, the connecting element can be secured to the anchor.

In one form, the systems and methods include at least one anchor engaged to the spinal column or other anatomical structures in a patient. A connecting element is engaged to an inserter instrument, and the inserter instrument is movable by the surgeon under electronic guidance to position the connecting element adjacent to the anchor. A targeting device and a tracking device are coupled to respective ones of the anchor and connecting element, and provide data regarding the relative positions of the connecting element and anchor to a processing subsystem. The processing subsystem processes the positional data and is coupled to a feedback system that relays the positional data to the surgeon, thereby enhancing the surgeon's ability to accurately guide the connecting element to the target location of the anchor through tissue of the patient.

In a further form, the connecting element includes a motion sensor that provides data regarding movement of the connecting element through the tissue. Movement of the connecting element along its insertion path is compared to a target trajectory between the connecting element and the anchor. If the trajectory of the insertion path deviates from the target trajectory between the connecting element and the anchor, the processor calculates suggested movements of the connecting element to align the connecting element along the target trajectory. The feedback system provides the surgeon with suggested movements from the insertion path location to align the connecting element along the target trajectory.

In a further form, the systems and methods include at least one anchor engageable to at least one vertebral body or other anatomical structures, and an extension extending proximally from at least one anchor to a proximal end of the extension. An inserter instrument includes a connecting element engaged thereto, and is operable to position the connecting element through tissue to a location adjacent to the at least one anchor with neither the inserter nor the connecting element mechanically engaged nor electronically associated with the extension as the connecting element is positioned in the body of the patient. The connecting element and anchor include an electronic guidance system that provides feedback to the surgeon regarding the relative positioning of the connecting element and the anchor as the connecting element is advanced through the tissue for implantation at the anchor.

In yet another form, the systems and methods include three or more anchors engageable to respective ones of three or more vertebral bodies or other anatomical components, and extensions extending proximally from respective ones of the anchors to a proximal end of the respective extension. An inserter instrument includes a connecting element engaged thereto, and at least one of the three or more anchors, and the connecting element include an electronic guidance system that is operable to provide feedback regarding the relative positioning between the connecting element and the at least one anchor as the connecting element is advanced through tissue and serially between locations adjacent the at least three anchors.

The electronic guidance system includes at least one targeting device associated with at least one anchor and a tracking device associated with the connecting element. It is contemplated that targeting device can be coupled to one or more of the anchors, the anchor extensions, or possibly both. The targeting devices can be an integral part of or embedded with the anchors and/or anchor extensions to remain implanted in the patient after the procedure. The targeting devices can also be removably associated with the anchors and/or anchor extensions for removal after the procedure. The tracking device can be an integral part of or embedded with the connecting element for implantation in the patient after the procedure, removably coupled to the connecting element and/or the inserter instrument for removal after the procedure, or a part of the inserter instrument. When embedded or forming an integral part of the anchor or connecting element, the targeting and/or tracking devices can be employed in subsequent procedures to determine the relative locations of the connecting element and anchor. Implanted targeting and tracking devices can also be used to determine the relative locations of the connecting element and anchors to other implants, objects, instruments and anatomical features in the patient after the procedure, thereby facilitating post-operative evaluation of the condition and location of the implanted devices and planning for any subsequent revision procedures. Removable targeting and/or tracking devices can be re-used in other procedures after sterilization, or may alternatively be discarded.

In one form, the electronic guidance system includes a targeting device that is one of an anode or cathode, and a tracking device that is oppositely charged from the targeting device. Current is applied to the connecting element tracking device, and the tissue between the connecting element tracking device and the anchor targeting device provides a conductive path for electric current flow therebetween such that the connecting element tracking device and anchor targeting function as an anode and cathode with the tissue completing the electrical circuit. As the connecting element approaches the anchor, the resistance provided by the tissue along the current path decreases, thereby allowing current flow between the targeting device and tracking device to increase. The current data is transmitted to a processing subsystem of the electronic guidance system, which in turn analyzes the current data and provides an output to a feedback device. The feedback device provides one or more of an audible, visual and tactile indication to the surgeon that the connecting element is moving toward the target location or away from the target location. The insertion data is used by the surgeon to move the connecting element along an insertion path that corresponds to a desired trajectory toward the anchor. The surgeon can make appropriate adjustments in the trajectory of the insertion path of the connecting element during its insertion to move the connecting element toward the target location at the anchor.

In one embodiment, the anchor is charged with an electrical charge at the target location, while adjacent portions of the anchor are shielded with opposite electrical charges so that the current flow between the connecting element and the anchor is focused to the target location and not shunted to tissue or other objects surrounding the anchor.

In another embodiment, the targeting device of the anchor includes alternating current to create an electrical field around the anchor. A ground is situated at the target location of the anchor so that intensity of the electrical field is reduced or eliminated at the target location. The connecting element includes an impedance sensor or magnetic sensor tracking device that influences the intensity of the electrical field around the anchor when the connecting element deviates from a trajectory directed toward the target location. Data regarding fluctuations in the intensity of the electrical field is transmitted by the transmitting device to the data processing subsystem, which analyzes the data to produce an output of the relative position between the connecting element and the anchor. The output is communicated with the surgeon with the feedback device by one or more of audible, visual, and tactile feedback so the surgeon can make appropriate adjustments in the insertion path of the connecting element and to align it with the target location of the anchor.

The present invention is generally directed to systems and methods for performing minimally-invasive surgical procedures in a patient. In one form of the present invention, the minimally-invasive surgical procedures include the use of at least one anchor engaged to tissue associated with various anatomical structures. For purposes of the present invention, the term "tissue" broadly refers to both soft tissues and bony tissues. Soft tissues include, for example, muscle tissues, vascular or heart tissues, ligament tissues, organ tissues, neural or brain tissues, or any other type of soft tissue that would occur to one of ordinary skill in the art. Bony tissues include, for example, skeletal tissues associated with long bones or other types of bones, spinal tissues associated with vertebral structures and components, cartilage tissues, tooth tissues, or any other type of bony tissue that would occur to one of ordinary skill in the art.

Figure 1:
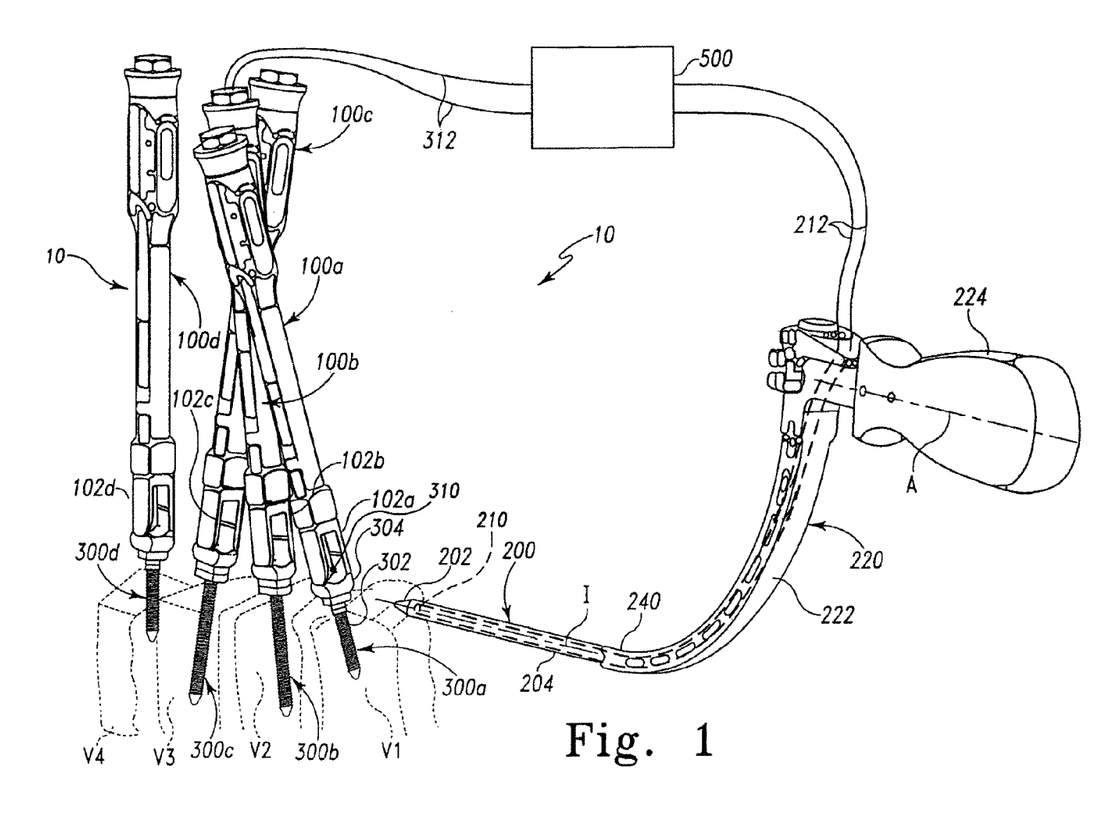
FIG. 1 is a perspective view of a system including anchors, anchor extensions, an inserter instrument and a connecting element, along with an electronic guidance system associated with at least one of the anchors and the connecting element.

Referring now to FIG. 1, shown therein is a minimally-invasive surgical system 10 that includes an inserter instrument 220, four anchor extensions 100a, 100b, 100c, 100d (collectively and individually referred to herein as anchor extensions 100) and an elongated connecting element 200. Anchor extensions 100a, 100b, 100c, 100d are releasably mountable to respective ones of the anchors 300a, 300b, 300c, 300d (collectively and individually also referred to herein as anchors 300.) Anchors 300a, 300b, 300c, 300d are engaged to respective ones of the vertebrae V1, V2, V3, V4. In one procedure, anchors 300 are engaged to the pedicles of the vertebrae, and surgical system 10 includes an inserter instrument 220 that is used in guiding connecting element 200 to anchors 300 through tissue of the patient, thereby eliminating the need to cut and/or retract the intervening musculature and nervature associated with the posterior spine, while also assisting the surgeon in quickly and accurately positioning the connecting element in the desired position relative to anchors 300. Extensions 100 can include a length extending proximally from the respective anchors 300 so that at least the proximal ends thereof are located outside a corresponding wound or incision in the patient through which a respective one of the anchors 300 is positioned to engage the respective vertebra. Surgical system 10 also has applications in procedures where one or more of anchors 300 lacks any extension 100 coupled thereto.

Figure 2:
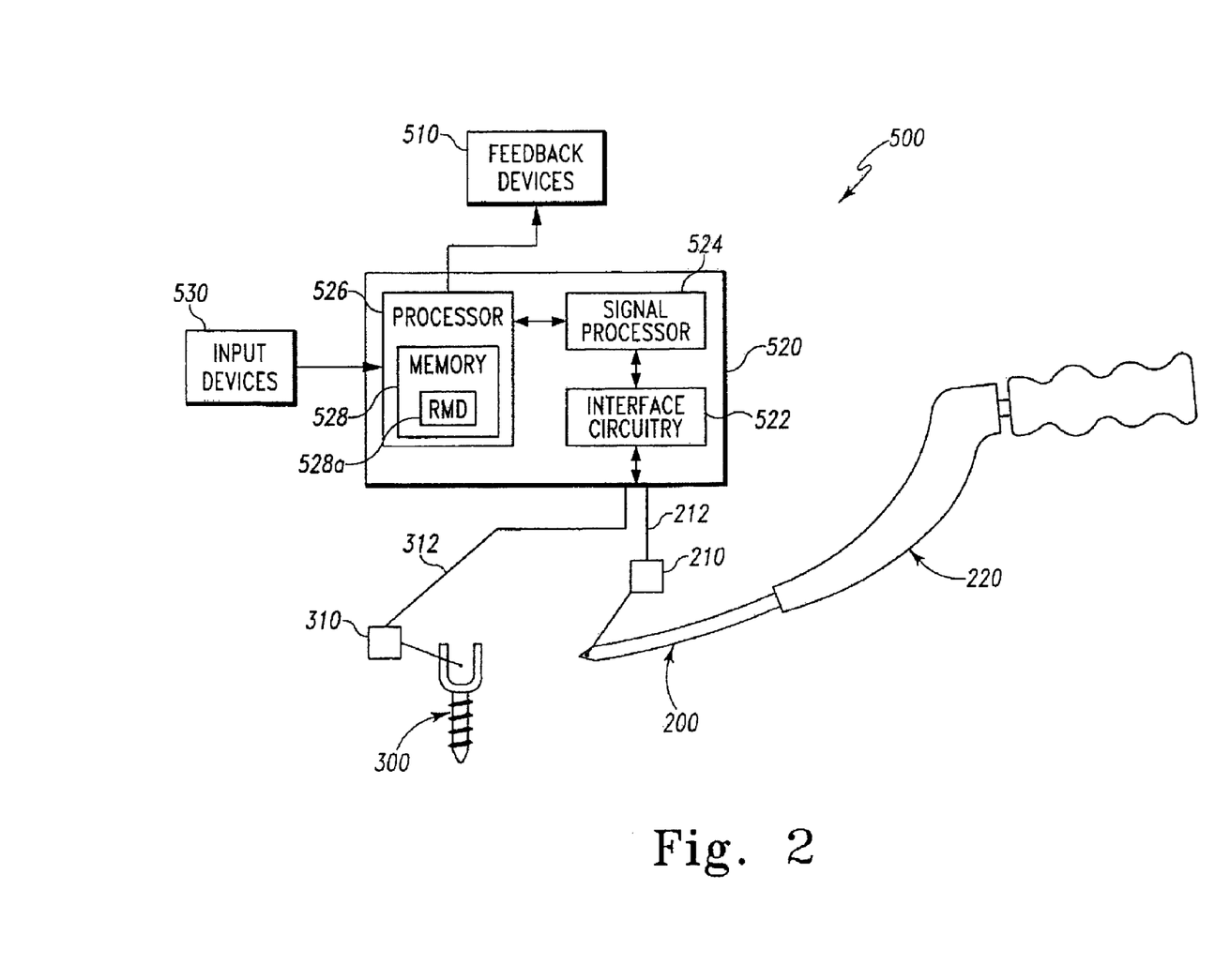
FIG. 2 is a diagrammatic view of a portion of the system of FIG. 1 showing one embodiment of an electronic guidance system.

Surgical system 10 further includes a guidance system 500 associated with one or more of the anchors 300 and connecting element 200 to assist the surgeon in guiding connecting element 200 through tissue of the patient to one or more of anchors 300 in the minimally-invasive procedure. As also shown in FIG. 2, surgical system 10 includes a tracking device 210 associated with connecting element 200, and a targeting device 310 associated with anchor 300. Targeting device 310 provides an indication of the target location of anchor 300 to which connecting element 200 is to be positioned. Tracking device 210 electronically communicates with targeting device 310 through the tissue of the patient to create a signal indicative of relative positioning between connecting element 200 and the target location of anchor 300 as the connecting element 200 is displaced through the tissue. Tracking device 210 is connected with a processor subsystem 520 of guidance system 500 via a communications link 212, and targeting device 310 is connected with the processor subsystem 520 of guidance system 500 via a communications link 312.

Guidance system 500 further includes processing subsystem 520 for processing signals and data received from one or both of tracking device 210 and targeting device 310. Guidance system 500 may further include one or more feedback devices 510 to communicate relative position data of connecting element 200 and anchor 300 to the surgeon or user. Feedback device 510 may be linked with processing subsystem 520 and operate as a function of a processor output signal which is generated in response to the signal from the tracking and targeting devices 210, 310 associated with connecting element 200 and anchor 300, respectively. In one form, feedback device 510 may include one or more visual markers in the form of a light, a light emitting diode (LED), fluorescent, incandescent, and/or neon output, and other light sources. In each form, the relative location and/or approach of connecting element 200 toward anchor 300 may be indicated by, for example, a discrete yes/no indicator, a color change, a flashing sequence, or other change in indicator state. In alternative forms, feedback device 510 may provide an output indicating the distance between connecting element 200 and anchor 300 in the form of a colorimetric strip, an aural/audio signal, or a digital display of distance and angle of approach. For embodiments with feedback device 510, feedback device 510 may be structured to provide information in addition to a positive or negative indication of whether connecting element 200 is approaching anchor 300, such as the distance the connecting element is inserted, angular orientation of the connecting element, deviation of the connecting element from a target insertion path, and the rate of insertion of the connecting element. Other embodiments contemplate that feedback device 510 can be of a Cathode Ray Tube (CRT) type, Liquid Crystal Display (LCD) type, plasma type, Organic Light Emitting Diode (OLED) type, or other types feedback devices. Alternatively or additionally, one or more other operator output devices can be utilized, such as, for example, a printer, one or more loudspeakers, or headphones.

Guidance system 500 can also include one or more communication interfaces suitable for connection to a computer network, such as, for example, a Local Area Network (LAN), a Municipal Area Network (MAN), a Wide Area Network (WAN) like the Internet, a medical diagnostic device, another therapeutic device, a medical imaging device, a Personal Digital Assistant (PDA) device, a digital still image or video camera, and/or an audio device. Guidance system 500 can also be arranged to show other information under control of the surgeon or user.

Processing subsystem 520 may include interface circuitry 522 of the analog type or digital type, Digital Signal Processor (DSP) 524, data processor 526, and memory 528. Interface circuitry 522 can be responsive to control signals from DSP 524 to provide corresponding analog stimulus signals to inserter instrument 200. At least one of interface circuitry 522 and DSP 524 may include one or more digital-to-analog converters (DAC) and one or more analog-to-digital converters (ADC) to facilitate operation of guidance system 500 in the manner described herein. Processor 526 can be coupled to DSP 524 to bidirectionally communicate therewith, selectively provide output to feedback device 510, and selectively respond to input from operator input device 530.

DSP 524 and/or processor 526 can be of a programmable type, a dedicated, hardwired state machine, or a combination thereof. DSP 524 and processor 526 perform in accordance with operating logic that can be defined by software programming instructions, firmware, dedicated hardware, a combination of these, or in a different manner as would occur to those skilled in the art. For a programmable form of DSP 524 or processor 526, at least a portion of the operating logic can be defined by instructions stored in memory 528. Programming of DSP 524 and/or processor 526 can be of a standard, static type, an adaptive type provided by neural networking, expert-assisted learning, fuzzy logic, or any combination thereof.

Memory 528 is illustrated in association with processor 526; however, memory 528 can be separate from or at least partially included in one or more of DSP 524 and processor 526. Memory 528 includes at least one Removable Memory Device (RMD) 528a. Memory 528 can be of a solid-state variety, electromagnetic variety, optical variety, or any combination thereof. Furthermore, memory 528 can be volatile, nonvolatile, or a mixture thereof. Memory 528 can be at least partially integrated with circuitry 522, DSP 524 and/or processor 526. RMD 528a can be a floppy disc, cartridge, or tape form of removable electromagnetic recording media, an optical disc, such as a CD or DVD type, an electrically reprogrammable solid-state type of nonvolatile memory, and/or other varieties as would occur to those skilled in the art. In still other embodiments, RMD 528a may be eliminated.

Circuitry 522, DSP 524, and processor 526 can be comprised of one or more components of any type suitable to operate as described herein. Further, it should be appreciated that all or any portion of circuitry 522, DSP 524, and processor 526 can be integrated together in a common device, and/or provided as multiple processing units. For a multiple processing unit form of DSP 524 or processor 526, distributed, pipelined and/or parallel processing can be utilized as appropriate. In one embodiment, circuitry 522 is provided as one or more components coupled to a dedicated integrated circuit form of DSP 524, processor 526 is provided in the form of one or more general purpose central processing units that interface with DSP 524 over a standard bus connection, and memory 528 includes dedicated memory circuitry integrated within DSP 524 and processor 526, and one or more external memory components including a removable disk form of RMD 528a. Circuitry 522, DSP 524, and/or processor 526 can include one or more signal filters, limiters, oscillators, format converters (such as DACs or ADCs), power supplies, or other signal operators or conditioners as appropriate to operate guidance system 500 in the manner described herein.

In one embodiment, connection links 212, 312 include the form of a flexible cable with opposite ends having one end electrically connected to equipment of guidance system 500. Links 212, 312 extend from the equipment to an opposite end connected with respective ones of the signal devices 210, 310. Connection links 212, 312 may include forms in addition to or alternative to a flexible cable, including one or more wires, cords, wireless links, infrared components, bluetooth, and/or other communication links. Further, it should be appreciated that other components, devices, and systems can be integrated into guidance system 500, such as, for example, an endoscope system, a catheterization system, an imaging system, a lighting system and/or a video camera system. Connection link 212 can be coupled to tracking device 210, connecting element 200 and/or inserter instrument 220. Connection link 212 can be removably coupled to one or more of these components, or permanently fixed relative to one or more of these components. Connection link 312 can be coupled to targeting device 310, anchor 300 and/or anchor extension 100. Connection link 312 can be removably coupled to one or more of these components, or permanently fixed relative to one or more of these components.

Figure 3:
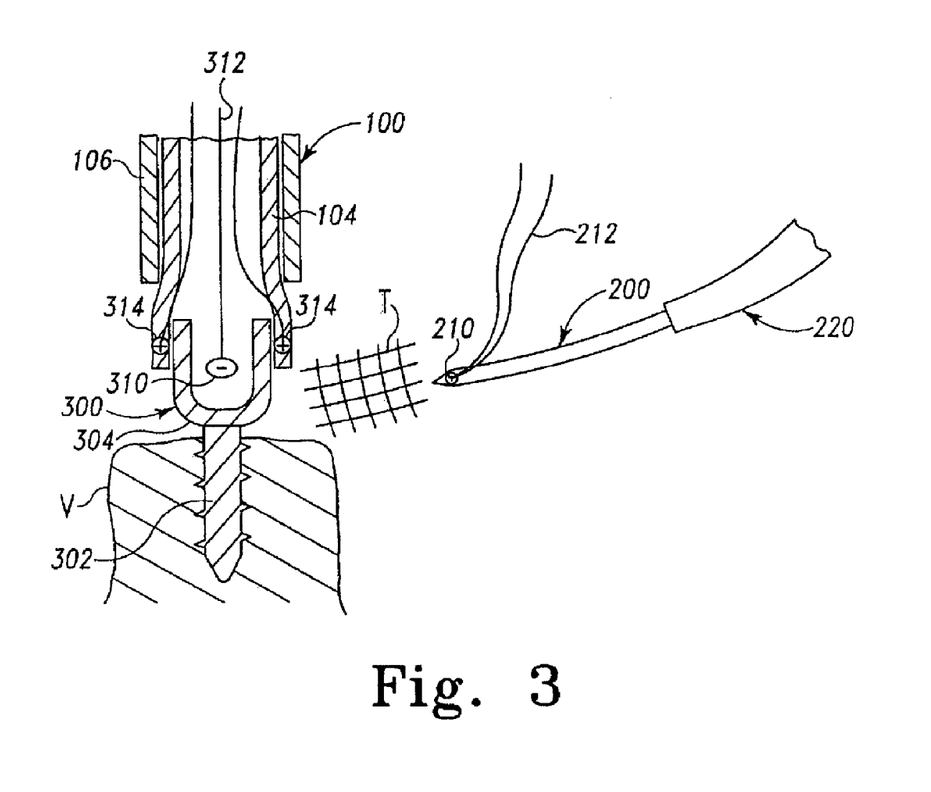
FIG. 3 is a partial cross-sectional view of an anchor and an anchor extension of the system of FIG. 1 and a connecting element extending from a distal portion of the inserter instrument, with respective portions of an electronic guidance system associated therewith.

In use, inserter instrument 220 is movable along a percutaneous insertion path that starts at a location remote from the extensions 100 and/or anchors 300, and extends through skin and tissue of the patient to position connecting element 200 at a location adjacent to one or more of the anchors 300. Inserter instrument 220 is operable to position connecting element 200 with neither connecting element 200 nor inserter instrument 220 mechanically engaged or mechanically associated with any of the extensions 100, at least during initial insertion. However, mechanical engagement and/or association of inserter instrument 220 with extensions 100 is not precluded. As shown in FIG. 3, during insertion, tracking device 210 and targeting device 310 provide an anode/cathode type arrangement so that electric current is transmitted therebetween through tissue T of the patient. As tracking device 210 approaches targeting device 310, the resistance to the current flow provided by the tissue is reduced, and the increase in the current flow provides an indication that connecting element 200 is approaching the target location of anchor 300 identified by targeting device 310. Conversely, if connecting element 200 is moved away from the target location of anchor 300, current flow between tracking device 210 and targeting device 310 is reduced via the increased resistance provided by the greater mass of tissue between tracking device 210 and targeting device 310. Links 212, 312 can be employed to supply the electrical current necessary to establish the electrical circuit between devices 210, 310, and also transmit information regarding the current flow to processing subsystem 520. This data is then analyzed by processor 526 and is communicated to the surgeon or user during insertion of connecting element 200 so that the surgeon or user can make appropriate adjustments to the insertion path of connecting element 200.

In a further embodiment, it is contemplated that one or more portions of extension 100 and/or anchor 300 adjacent to targeting device 310 is shielded with oppositely charged nodes 314. Oppositely charged nodes 314 completely or partially surround the target location, with electrical charges opposite that of the target location to prevent unintended dissipation of the charge of targeting device 310 into surrounding tissue. In a further embodiment, oppositely charged nodes 314 are at different voltages than the charge of tracking device 210 in order to create a more favorable current flow between targeting device 310 and tracking device 210.

In one embodiment, anchor 300 is made from a conductive material so that it conducts electric current, thereby allowing anchor 300 to constitute the electrically charged targeting device 310. All or a portion of anchor 300 and/or extension 100 can be insulated or shielded to direct current flow from the tissue through a non-insulated target location. In another embodiment, anchor 300 is made from a non-conductive or poorly conductive material, and targeting device 310 is an electrode or other electrically charged structure that is electrically coupled to a current source or in a current flow path. In still other embodiments, targeting device 310 is a separately charged electrode positioned in the target location defined by anchor 300, but is not a part of anchor 300.

Connecting element 200 can be an elongated brace, rod or shaft that is generally linear or curved along its length to facilitate placement between three or more anchors. In one embodiment, connecting element 200 is made from a conductive material so that it conducts electric current, thereby allowing the connecting element 200 to constitute the electrically charged tracking device 210. All or a portion of connecting element 200 can be insulated or shielded to direct current flow through leading end 202. In another embodiment, connecting element 200 is made from a non-conductive or poorly conductive material, and tracking device 210 is an electrode or other electrically charged structure at the leading end of connecting element 200 that is electrically coupled to a current source or to a current path.

Other embodiments contemplate that connecting element 200 can be curved along all or a portion of its length. It is also contemplated that connecting element 200 can include any known configuration for a rod, implant, or fastener, so long as connecting element 200 is insertable using inserter instrument 220 and engageable to at least one of the anchors 300. Further, connecting element 200 can be non-rigid, elastic and/or super-elastic and in the form of a cable, band, wire, or artificial ligament that is used in tethering, guiding, or other surgical procedures. Connecting element 200 can be percutaneously or non-percutaneously inserted with inserter instrument 220 to a location adjacent one or more of anchors 300 when anchor 300 is engaged to an anatomical structure in the body of the patient.

In the illustrated embodiment, connecting element 200 is a rigid, linear rod that forms an extension of inserter arm 222 of inserter instrument 220 along an axis I defined by connecting element 200. However, it is contemplated that connecting element 200 can have one or more offset portions and/or a curvature that varies or is compounded along its length. In the illustrated embodiment, inserter instrument 220 includes a handle portion 224 at a proximal end of inserter arm 222 that extends along an axis A (FIG. 1). In one embodiment, axis A is generally parallel to axis I, and inserter arm 222 is curved between handle portion 224 and connecting element 200. Other arrangements between handle portion 224 and inserter arm 222 are also contemplated, including arrangements where axis A is obliquely oriented to, orthogonal to, or an extension of axis I.

Connecting element 200 (FIG. 1) is inserted via the inserter instrument 220 to a location adjacent anchors 300 where connecting element 200 can be engaged to anchors 300 to stabilize the respective vertebrae V1, V2, V3 and V4. In addition to the use of electronic guidance system 500, insertion of connecting element 200 can be guided by fluoroscopic imaging techniques, tactile feel and indications, mechanical coupling arrangements, and/or other suitable arrangements. Examples of imaging techniques are disclosed, for example, in U.S. Pat. No. 6,226,548, the contents of which are incorporated herein by reference in their entirety.

In FIG. 1, the leading end 202 of connecting element 200 is shown in an approach to anchor 300a, with trailing end 204 of connecting element 200 engaged to a distal end 240 of inserter arm 222. Extension 100a forms a space 102a adjacent anchor 300a for receiving connecting element 200. By grasping handle portion 224, the surgeon can manipulate leading end 202 and connecting element 200 through the tissue of the patient and through space 102a toward space 102b formed between extension 100b and anchor 300b for placement there through, with feedback being provided to the surgeon with electronic guidance system 500 to guide insertion of connecting element 200. Serial advancement of connecting element 200 through spaces 102c and 102d formed between extensions 100c and 100d and the respective anchors 300c, 300d can continue so that connecting element 20 can be secured to each of the anchors. When connecting element 200 is positioned between the desired number of anchors, connecting element 200 is engaged to the anchors with a suitable engaging member, such as a set screw, nut, cap, or other types of engaging members. In a further embodiment, connecting element 200 is seated relative to the anchors by operation of one or more of the extensions 100 before engaging connecting element 200 to anchors 300. Such seating can take the form of a spinal reduction procedure where one or more vertebrae are pulled and/or moved into alignment with one another, and then engaged and maintained in such alignment by engagement of connecting element 200 thereto via the anchors 300.

In one embodiment, as shown in FIG. 3, one or more of the extensions 100a-100d each include a first member 104 for engaging the respective anchor 300, and a second member 106 movable relative to first member 104 to secure anchor 300 to anchor extension 100. In some embodiments, one or more anchor extensions 100 are configured such that second member 106 can reduce or seat connecting element 200 for engagement with one or more of the anchors 300. After connecting element 200 is placed in the respective space 102 between the anchor and the respective extension, the one or more anchor extensions 100 with reduction capability can be manipulated so that the second member 106 and the anchor 300 move relative to one another to seat the connecting element 200 relative to anchor 300. Engaging members can be delivered through the respective extensions to engage the connecting element 200 to the respective anchors 300.

Anchors 300 include a tissue engaging portion 302 and a connecting element engaging portion 304. In the illustrated embodiment, tissue engaging portion 302 is a bone screw, including a threaded shank to engage the bony structure of an underlying vertebra V. Connecting element engaging portion 304 can constitute a receiver having a U-shape formed by a pair of opposing arms defining a longitudinal passage alignable along insertion axis I so as to form the target location to receive connecting element 200. The arms further define a proximal/distally extending opening that opens at a proximal end of the arms to receive a set screw (not shown) to secure connecting element 200 in the passage with connecting element 200 extending from the respective anchor 300 along insertion axis I. Tissue engaging portion 302 can be pivotally received in or coupled to connecting element engaging portion 304 through a distal opening thereof, and structured to interact therewith to provide anchor 300 with multi-axial capabilities that permits either a selected number of positions or an infinite number of positions of tissue engaging portion 302 relative to connecting element engaging portion 304.

Other forms of anchors 300 are also contemplated, including uni-axial and uni-planar bone screws. The bone engaging portion 302 can be in the form of a spike, staple, fusion device, cannulated screw, fenestrated screw, interbody device, intrabody device, clamp, plate, suture anchor, bolt, pin or other bone engaging member. The connecting element engaging portion 304 can be in the form of a saddle, yoke, eye-bolt or through-hole, side opening member, bottom opening member, top-opening member, eyelet, or any other structure engageable with the connecting element.

Various minimally-invasive surgical procedures and techniques can be completed via the use of system 10. One type of surgical technique is directed to spinal surgery for positioning an elongated connecting element along one or more vertebral levels to provide spinal stabilization. A number of anchors 300 are selected according to the number of vertebral levels to be instrumented or corrected. For example, a single level procedure may include an anchor engaged to each of two vertebrae, or a two level procedure may include an anchor engaged to each of three vertebrae.

When the desired number of levels has been selected, anchors 300 are engaged to the respective vertebrae. In posterior spinal surgical techniques, the anchors 300 can constitute screws engaged in the pedicles of the vertebrae. Anchors 300 can be positioned into the patient through one or more minimally-invasive access portals, formed by, for example, an incision, cannula, or retractor system. Extensions 100 can be clamped to the anchors after the anchors are engaged to the vertebrae. Alternatively, the anchors can be clamped to the extensions, and then delivered through the access portal or portals for engagement with the respective vertebrae. Placement of the anchors can be facilitated, for example, via a guide wire, image guided surgery system, fluoroscopic imaging, computer assisted surgical navigation, X-rays, CT scans, endoscopic viewing systems, microscopic viewing systems, loupes, and/or naked eye visualization.

With the anchors 300 engaged to the vertebrae and with extensions 100 extending therefrom, extensions 100 have a length sufficient to extend outside of the patient so that the proximal ends of the extensions 100 are accessible for grasping and pivoting, or application of forces to facilitate alignment of the connecting element engaging portions 304 of the anchors 300. For example, distraction, compression or torsional forces can be provided to one or more of the extensions 100 to provide a desired effect to the vertebrae either before of after placement of the connecting element between the anchors. In other techniques, extensions 100 are not provided or not attached to one or more of anchors 300.

Figure 4:
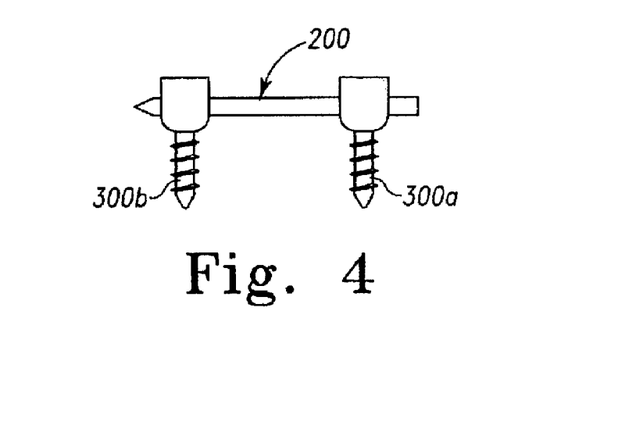
FIG. 4 is a portion of the system of FIG. 1, with the connecting element positioned between at least two anchors.

Connecting element 200 can enter the patient percutaneously or through a retracted opening from an entry location remote from anchors 300. Connecting element 200 is guided by the surgeon through the tissue to a location adjacent the nearest anchor 300 and into the target location defined thereby. The connecting element can then be serially advanced through the other target locations, such as spaces 102, defined by the other anchors 300 to extend between two or more anchors engaged to two or more vertebrae (FIG. 4). Insertion of connecting element 200 is facilitated via the electronic guidance system 500. Electronic guidance system 500 includes one or more tracking devices 210 provided in or on the connecting element 200, and one or more targeting devices 310 associated with the targeted insertion location for connecting element 200 provided by one or more of the anchors 300. The tracking and targeting devices 210, 310 function to track and provide relative positional data of the connecting element and the target location of the anchor during insertion of connecting element 200 into the patient. It is further contemplated that the leading end of connecting element 200 can be tapered or pointed to facilitate puncture and/or tunneling through the skin and tissue of the patient, either to form a path or to be inserted along a path formed by a trocar or other device.

Connecting element 200 can be remotely disengaged from inserter instrument 220 by manipulating inserter instrument 220 to release it from connecting element 200. Inserter instrument 220 can then be withdrawn from the patient by pulling it with handle portion 224 in the reverse direction along the insertion path. Set screws or other engaging members can be delivered to anchors 300 with a driving instrument, and engaged with respective ones of the anchors 300 to secure connecting element 200 to anchors 300. Extensions 100 can then be released and removed from the respective anchors 300.

One or more other connecting elements can be similarly engaged to the spinal column along the same vertebral level or levels, or along other vertebral levels. Other procedures can also be completed in conjunction with the stabilization procedure, including discectomy, interbody fusion, artificial disc replacement, bone removal, tissue removal, intravertebral reduction, joint replacement, annular repair, and/or any other spinal surgical procedures.

Tracking and targeting devices 210, 310 are structured to communicate with one another electronically through the tissue of the patient so that processing subsystem 520 can determine the location of connecting element 200 relative to anchor 300. It should be appreciated that in alternative forms, tracking and targeting devices 210, 310 may be placed external to one or both of connecting element 200 and anchor 300, embedded or internally located relative one or both of connecting element 200 and anchor 300, or partially internal and partially external relative to one or both of connecting element 200 and anchor 300.

Figure 5:
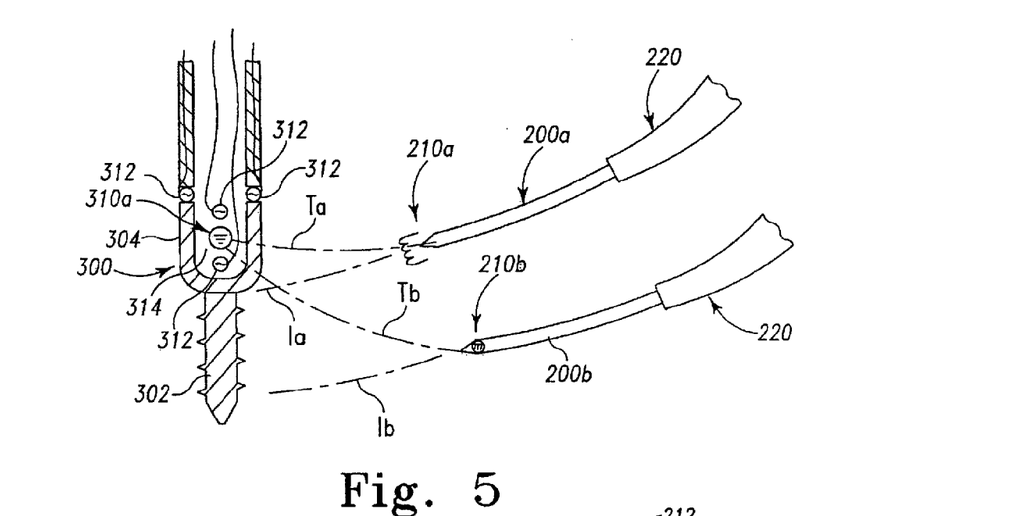
FIG. 5 is a partial cross-sectional view of another embodiment of an anchor and anchor extension of the system of FIG. 1, and an elevational view of another embodiment of a connecting element along with associated portions of another embodiment of an electronic guidance system.

Referring to FIG. 5, shown therein is another embodiment of guidance system 500 includes the tracking and targeting devices. Anchor 300 includes alternate targeting device 310a, which in turn includes alternating current signals 312 around the target location 314, which is grounded. Alternating current signals 312 generate an electric field with distinct frequency bands around target location 314. Connecting element 200a includes an impendence sensor 210a. In another alternative form, connecting element 200b includes a magnetic sensor 210b. As connecting element 210a or 210b is positioned through the tissue, changes in current amplitude or frequency magnitude on the circuit including alternating current signals 312 are measured and sent to processor subsystem 520. These changes are measured and provide an indication of whether connecting element 210a, 210b is getting closer to target location 314. Furthermore, the direction of deviation of the insertion path Ia, Ib from the target insertion path Ta, Tb can be noted by registering the source frequency changes to particular directions. The directional deviation information can be processed by processor subsystem 520 and provided to the surgeon so that the insertion path of connecting element 200a, 200b can be adjusted along the respective target path Ta, Tb, respectively.

As an alternative or additional sensing mechanism, electromagnetic radiation is used to sense the location of connecting element 200 relative to anchor 300 by returning, blocking, and/or dispersing the radiation in a manner that can be detected and identified as being indicative of the location of connecting element 200. In a specific implementation of this alternative approach, connecting element 200 is directed along a path such that a light beam directed across the path is broken/blocked when connecting element 200 travels along such path. As a result, the output signal from an optical detector responsive to the light beam changes state, indicating the presence of the connecting element. Likewise, acoustic energy, such as ultrasound, may be used to detect the location of connecting element 200 relative to anchor 300.

Figure 6:
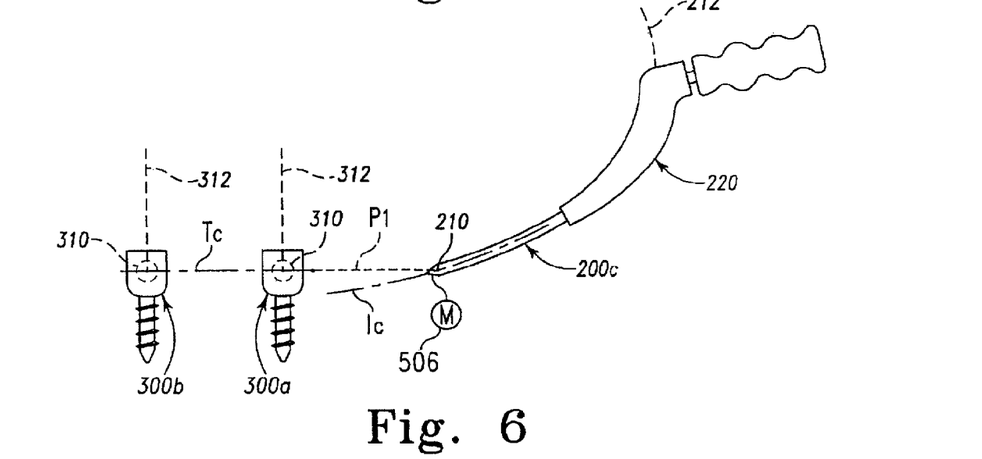
FIG. 6 is an elevational view of a pair of anchors and a connecting element along with associated portions of another embodiment of an electronic guidance system.

In still another embodiment of guidance system 500, as shown in FIG. 6, connecting element 200c is provided with a motion sensor 506. Motion sensor 506 can include any one or combination of accelerometers, optical sensors, electromagnetic sensors, radio-frequency emitters, and angular sensors, for example. Motion sensor 506 provides data regarding at least one of the direction and distance of movement of connecting element 200c, along with the relative positional data between connecting element 200c and the target location of one or more of anchors 300a, 300b determined according to the tracking and targeting devices discussed hereinabove. The motion data and relative positional data can be sent to processor subsystem 520 and used to calculate an actual insertion path Ic and a target insertion path Tc. The actual insertion path deviation from the target insertion path is calculated. Suggested adjustments to the actual insertion path Ic can be provided to the surgeon to suggest movements that will align connecting element 200c along target insertion path Tc. The actual positional and trajectory data and calculated adjustments can be made and updated continuously during the insertion procedure so that the surgeon can use the feedback to optimize the insertion of connecting element 200 to the target location.

Figure 7:
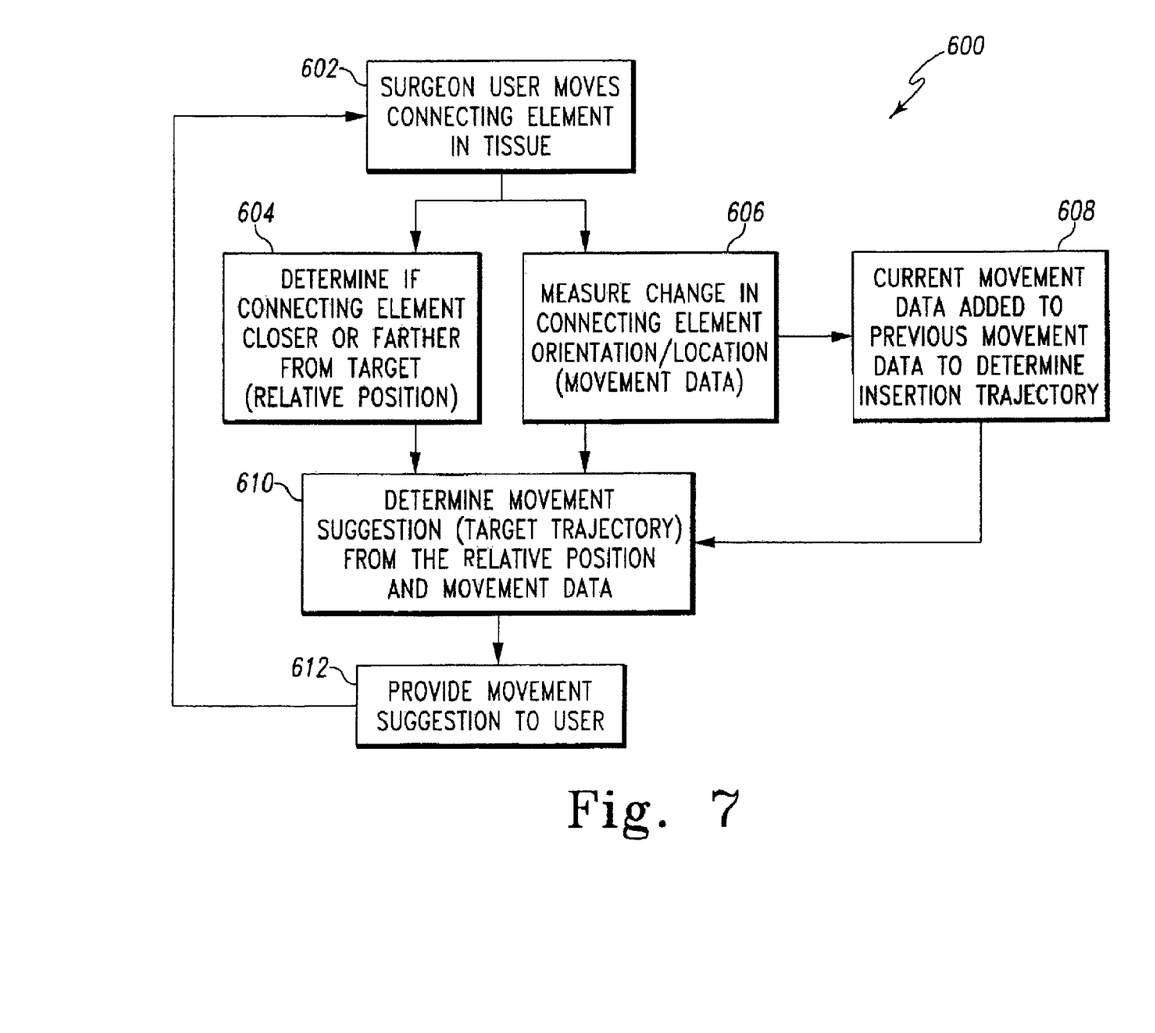
FIG. 7 is a flowchart of an algorithm for guiding the positioning of a connecting element into a patient to a desired location relative to at least one anchor implanted in the patient.

FIG. 7 illustrates an example of an algorithm programmable into processing subsystem 520 for carrying out a surgical method using the electronic guidance system with motion and relative position determinations to guide placement of the connecting element to a target location in the patient. Routine 600 begins at step 602 where a surgeon user moves the connecting element into tissue of the patient. The relative position between the connecting element and the target location associated with the anchor is determined at step 604. Using any of the targeting and tracking devices discussed herein, movement of the connecting element toward or away from the target location is measured and provided to processing subsystem 520 via one or both of the communication links 212, 312. Simultaneously at step 606, one or more motion sensors associated with the connecting element measure one or more of the change in the connecting element orientation, location or other desired movement data associated with the connecting element. At step 608, the currently measured movement data is added to previously measured movement data to determine an insertion path trajectory of the connecting element.

At step 610, a target trajectory between the connecting element and the target location associated with the anchor is calculated. This target trajectory is compared to the insertion path trajectory to determine a movement suggestion from the insertion path trajectory that would position the connecting element along the target trajectory. For example, the movement suggestion may include any one or combination of a direction, distance and angular adjustment of the connecting element to align it along the target trajectory. Routine 600 returns to step 602 to provide a continuous loop where the position data and movement data are updated to provide revised movement suggestions as the connecting element is moved through the tissue.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A system for minimally-invasive surgical procedures in a patient, comprising:
    at least one tissue anchor including a tissue engaging portion and a receiving portion coupled to said tissue engaging portion;
    an inserter instrument including a proximal handle portion and an inserter arm extending from said proximal handle portion;
    a connecting element for implantation in the patient, said connecting element releasably engaged to said inserter arm; and
    an electronic guidance system including a targeting device at said receiving portion of said at least one tissue anchor and a tracking device at said connecting element, said tracking device being operable to electrically communicate with said targeting device through tissue of the patient to provide an electronic signal that varies in accordance with a relative position between said connecting element and said receiving portion, said electronic guidance system further including a processor subsystem that receives said electronic signal, said processor subsystem being programmed to determine a change in a relative position between said receiving portion and said connecting element based on said electronic signal, said electronic guidance system further including a feedback device operable to communicate said change in said relative position as said connecting element is guided through tissue of the patient;
    wherein said connecting element includes a leading end and an opposite trailing end, said trailing end being coupled to said inserter instrument and said connecting element extending away from said trailing end to said leading end, said leading end including said tracking device and said tracking device includes one of an anode and a cathode;
    wherein said receiving portion including a target location to receive said connecting element and said targeting device is positioned at said target location, said targeting device including the other said anode and said cathode, wherein an electric current flow path is provided between said anode and said cathode through tissue of the patient when said leading end of said connecting element is in contact with tissue of the patient;
    wherein as said leading end of said connecting element approaches said at least one receiving portion electric current flow between said anode and said cathode increases and as leading end of said connecting element moves away from said receiving portion electric current flow between said anode and said cathode decreases;
    wherein said processing subsystem receives signals corresponding to said current flow and is programmed to determine said relative position of said leading end and said receiving portion based on said signals and provide data regarding said relative position to said feedback device; and
    wherein said target location includes shielding around said at least one tissue anchor to resist dissipation of current flow into adjacent tissue and to direct current flow to said one of said anode and said cathode at said target location.

2. The system of claim 1, wherein:
    said at least one tissue anchor comprises a bone anchor; and
    said tissue engaging portion comprises a bone engaging portion configured to engage bony tissue.

3. The system of claim 2, wherein:
    said connecting element is a rigid spinal rod having a body extending between a leading end and an opposite trailing end, said trailing end being engaged to said inserter arm and with said connecting element extending away from said inserter arm to said leading end; and
    said tracking device is provided at said leading end.

4. The system of claim 1, wherein:
    said at least one tissue anchor includes two or more tissue anchors; and
    two or more anchor elongated extensions, each of said anchor elongated extensions being releasably mounted to a corresponding one of said two or more tissue anchors.

5. The system of claim 4, wherein:
    said two or more tissue anchors comprise bone anchors; and
    said tissue engaging portion comprises a bone engaging portion configured to engage bony tissue.

6. The system of claim 1, wherein said feedback device communicates by at least one of visual and audible output.

7. The system of claim 1, wherein:
    said shielding includes an electrical charge around said targeting device that corresponds to an electrical charge of said one of said anode and said cathode of said tracking device, said electrical charge including a first voltage; and
    said tracking device includes an electrical charge with a second voltage that differs from said first voltage.

8. The system of claim 1, wherein:
    said connecting element includes a motion sensor connected thereto and said motion sensor is operable to detect data associated with movement of said connecting element through tissue of the patient;

said motion sensor is linked to said processor subsystem to communicate said movement data to said processor subsystem; and said processor subsystem is programmed to calculate a target insertion path for said connecting element to direct said connecting element toward said receiving portion.

9. A system for minimally-invasive surgical procedures in a patient, comprising:

at least one tissue anchor including a tissue engaging portion and a receiving portion coupled to said tissue engaging portion;

an inserter instrument including a proximal handle portion and an inserter arm extending from said proximal handle portion;

a connecting element for implantation in the patient, said connecting element releasably engaged to said inserter arm; and an electronic guidance system including a targeting device at said receiving portion of said at least one tissue anchor and a tracking device at said connecting element, wherein:

said targeting device is operable to generate an electrical field with distinct frequency bands around a target location at said receiving portion;

said tracking device includes a sensor operable to influence changes in said frequency bands as said connecting element is moved toward and away from said target location;

said electronic guidance system further including a processor subsystem and at least said targeting device is operable to communicate a signal corresponding to said changes in said frequency bands, said processor subsystem being programmed to determine a change in a relative position between said receiving portion and said connecting element based on said signal, said electronic guidance system further including a feedback device operable to communicate said change in said relative position as said connecting element is guided through tissue of the patient;

said connecting element includes a leading end and an opposite trailing end, said trailing end being coupled to said inserter instrument and said connecting element extending away from said trailing end to said leading end, said leading end including said tracking device and said tracking device includes one of an anode and a cathode;

said receiving portion including a target location to receive said connecting element and said targeting device is positioned at said target location, said targeting device including the other of said anode and said cathode, wherein an electric current flow path is provided between said anode and said cathode through tissue of the patient when said leading end of said connecting element is in contact with tissue of the patient;

wherein as said leading end of said connecting element approaches said at least one receiving portion electric current flow between said anode and said cathode increases and as leading end of said connecting element moves away from said receiving portion electric current flow between said anode and said cathode decreases;

wherein said processor subsystem receives signals corresponding to said current flow and is programmed to determine said relative position of said leading end and said receiving portion based on said signals and provide data regarding said relative position to said feedback device; and said targeting device includes shielding means around said target location, said shielding means for dissipating current flow in tissue around said target location.

10. The system of claim 9, wherein:
said at least one tissue anchor comprises a bone anchor; and
said tissue engaging portion comprises a bone engaging portion configured to engage bony tissue.

11. The system of claim 9, wherein said sensor is a magnetic sensor.

12. The system of claim 9, wherein said sensor is an impedance sensor.

13. The system of claim 9, wherein said target location at said receiving portion is grounded and said targeting device includes alternating current signals around said target location generating said electrical field.

14. A method of performing a minimally-invasive surgical procedure in a patient, comprising:

engaging at least one anchor to an anatomical structure;
providing a first electrical charge at a receiving portion of the at least one anchor, the receiving portion configured to receive a connecting element;
inserting the connecting element in tissue adjacent the anatomical structure;
providing the connecting element with a second electrical charge that is opposite the first electrical charge;
establishing current flow between the first and second electrical charges through the tissue;
measuring changes in the current flow as the connecting element moves through the tissue, wherein the current flow changes correspond to relative positional data between the connecting element and the receiving portion; and
changing a direction of movement of the connecting element through the tissue when the current flow decreases.

15. The method of claim 14, wherein the at least one anchor comprises a bone anchor and the anatomical structure comprises a spinal column;
wherein the engaging comprises anchoring the at least one bone anchor to a vertebra of the spinal column; and
wherein the method comprises a method of performing a minimally-invasive spinal stabilization procedure.

16. The method of claim 14, further comprising:
moving the connecting element through the tissue to position a leading end of the connecting element into the receiving portion of the at least one anchor.

17. The method of claim 14, further comprising:
shielding current flow into tissue around the receiving portion with shielding electrical charges around the receiving portion that are opposite the first electrical charge, wherein the shielding electrical charges and the second electrical charge are at different voltages.

18. The method of claim 14, wherein measuring changes in the current flow includes determining a relative position between a leading end of the connecting element and the receiving portion of the anchor.

19. A method of claim 14, further comprising:
determining an insertion path trajectory of the connecting element based on movement data during the inserting of the connecting element, wherein the movement data is determined by a motion sensor at the connecting element;
determining a target trajectory to position the connecting element in the receiving portion based on the relative positional data between the connecting element and the receiving portion; and
communicating changes in the insertion path trajectory to align the connecting element along the target trajectory.

20. A method of performing a minimally-invasive surgical procedure in a patient, comprising:
engaging at least one anchor to an anatomical structure, wherein the at least one anchor includes a target location;
inserting a leading end of a connecting element in tissue adjacent the anatomical structure;
determining a relative position between the leading end of the connecting element and the target location;
determining an insertion path trajectory of the connecting element based on movement data during inserting the connecting element, wherein the movement data is determined by a motion sensor associated with the connecting element;
determining a target trajectory to position the connecting element in the receiving portion based on the relative position between the connecting element and the receiving portion; and
communicating changes in the insertion path trajectory to align the connecting element along the target trajectory.

21. The method of claim 20, wherein the at least one anchor comprises a bone anchor and the anatomical structure comprises a spinal column;
wherein the engaging comprises anchoring the at least one bone anchor to a vertebra of the spinal column; and
wherein the method comprises a method of performing a minimally-invasive spinal stabilization procedure.

22. The method of claim 20, further comprising:
advancing the connecting element from the receiving portion of the at least one anchor into a receiving portion of a second anchor; and
securing the connecting element to the at least one anchor and the second anchor.

23. The method of claim 20, wherein determining the relative position between the leading end of the connecting element and the target location includes measuring a change in electrical current flow between the connecting element and the target location.

24. A system for minimally-invasive surgical procedures in a patient, comprising:
anchor means for engaging an anatomical structure in the patient, said anchor means including a receiving portion extending from the anatomical structure when said anchor means is engaged to the anatomical structure, wherein said receiving portion includes targeting means for providing a target location associated with the anchor means;
an inserter instrument including a proximal handle portion and an inserter arm extending from said proximal handle portion;
a connecting element for implantation through tissue of the patient, said connecting element releasably engaged to said inserter arm, wherein said connecting element includes tracking means electrically communicating with said targeting means for continuously generating an electric signal that varies according to a relative position between said targeting means and said tracking means; and
processing means for receiving said electrical signal and generating an output indicating changes in said relative position as said connecting element is advanced through tissue of the patient;
said connecting element includes a leading end and an opposite trailing end, said trailing end being coupled to said inserter instrument and said connecting element extending away from said trailing end to said leading end, said leading end including said tracking means and said tracking means includes one of an anode and a cathode;
said receiving portion including a target location to receive said connecting element and said targeting means is positioned at said target location, said targeting means including the other of said anode and said cathode, wherein an electric current flow path is provided between said anode and said cathode through tissue of the patient when said leading end of said connecting element is in contact with tissue of the patient;
wherein as said leading end of said connecting element approaches said at least one receiving portion electric current flow between said anode and said cathode increases and as leading end of said connecting element moves away from said receiving portion electric current flow between said anode and said cathode decreases;
wherein said processing means receives signals corresponding to said current flow and is programmed to determine said relative position of said leading end and said receiving portion based on said signals and provide data regarding said relative position to said feedback device; and
wherein said targeting means includes shielding means around said target location, said shielding means for dissipating current flow in tissue around said target location.

25. The system of claim 24, further comprising:
feedback means for communicating said changes in said relative position to a user as said connecting element is advanced through tissue of the patient.

26. The system of claim 24, wherein:
said connecting element further includes sensor means for measuring movement of said connecting element through the tissue of the patient; and
said processing means receives signals corresponding to said measured movement and said processing means includes means for determining a target trajectory based on said relative position between said targeting means and said tracking means, wherein said target trajectory positions said connecting element in said receiving portion when said connecting element is advanced through the tissue along the target trajectory.

27. The system of claim 24, wherein said target means includes means for generating an electrical field around said target location and said tracking means includes means for influencing said electrical field based on said relative position between said targeting means and said tracking means.

* * * * *